(12) United States Patent
Goldberg et al.

(10) Patent No.: US 7,749,487 B2
(45) Date of Patent: Jul. 6, 2010

(54) METHOD TO ASSESS SURFACTANT ADSORPTION ON SKIN

(75) Inventors: Jessica Weiss Goldberg, Fairfield, CT (US); Douglas Ryan Eli, San Antonio, TX (US); Suzanne Lynn Gencarelli, Milford, CT (US); Shauna Mary Lagatol, New Haven, CT (US); Robert Daniel Sabin, Newton, CT (US); Carol Kregler Vincent, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 601 days.

(21) Appl. No.: 11/373,795

(22) Filed: Mar. 10, 2006

(65) Prior Publication Data

US 2007/0212304 A1 Sep. 13, 2007

(51) Int. Cl.
*A61B 5/00* (2006.01)
(52) U.S. Cl. ..................................... 424/9.8
(58) Field of Classification Search .................. 424/9.8
See application file for complete search history.

(56) References Cited

U.S. PATENT DOCUMENTS

| | | | |
|---|---|---|---|
| 5,942,186 | A | 8/1999 | Sanada et al. |
| 5,958,560 | A | 9/1999 | Ewan |
| 6,074,721 | A | 6/2000 | Moore et al. |
| 6,669,929 | B1 * | 12/2003 | Boyd et al. .............. 424/49 |
| 2003/0107149 | A1 | 6/2003 | Yang et al. |
| 2004/0258896 | A1 | 12/2004 | Yang et al. |
| 2005/0031674 | A1 | 2/2005 | Redmond et al. |
| 2005/0037055 | A1 | 2/2005 | Yang et al. |
| 2005/0058613 | A1 | 3/2005 | Lange et al. |
| 2005/0232958 | A1 | 10/2005 | Lee |
| 2005/0249672 | A1 | 11/2005 | Bolbot |

FOREIGN PATENT DOCUMENTS

| | | |
|---|---|---|
| JP | 11 267105 A | 10/1999 |
| WO | 93/07862 | 4/1993 |
| WO | 94/13354 | 6/1994 |
| WO | 94/26218 | 11/1994 |
| WO | 02/087626 A | 11/2002 |
| WO | 2005/004989 | 1/2005 |

OTHER PUBLICATIONS

Academic Press Dictionary of Science and Technology, 1992, s.v. "compound," http://www.credoreference.com/entry/3088687 (accessed Mar. 31, 2008), 1 page.*
"Cumulative effect of surfactants on cutaneous horny layers: Adsorption onto human keratin layers in vivo", Genji lmokawa and Yutaka Mishimia, *Contact Dermatitis* 1979: 5: 357-366.
International Search Report. PCT/EP2007/001165, mailed Nov. 19, 2007, 3 pp.
Paye, Marc, et al., "Dansyl chloride labeling of stratum corneum: Its rapid extraction from skin can predict skin irritation due to surfactants and cleansing products." Contact Dermatitis, vol. 30, No. 2. 1994, pp. 91-96, XP001095239.
Sauermann, G., et al., "Comparative Study of Skin Care Efficacy and In-Use Properties of Soap and Surfactant Bars", Journal of the Society of Cosmetic Chemists, vol. 37, No. 6, 1986, pp. 309-327, XP001094733.

* cited by examiner

*Primary Examiner*—Frederick Krass
*Assistant Examiner*—Gigi Huang
(74) *Attorney, Agent, or Firm*—Alan A. Bornstein

(57) ABSTRACT

A convenient to use test method for comparing the relative affinity of surfactants for the skin employs a solid or semisolid matrix for associating a dye or pigment with the skin. The dye or pigment has an affinity to either the skin or a surfactant adsorbed on the skin during personal cleansing. The matrix may include a reagent soluble polymer film or temporary tattoo.

11 Claims, 4 Drawing Sheets

Note: Black rings superimposed on image to delineate treated/stained areas

METHOD TO ASSESS SURFACTANT ADSORPTION ON SKIN

BACKGROUND OF THE INVENTION

1. Field of the Invention

The invention relates to a test method for estimating the level of residual surfactant on the skin.

2. The Related Art

Personal cleansing products are frequently marketed based on their degree of mildness to the skin of the user. Unfortunately, many surfactants in common use tend bind to the skin proteins, which can result in skin irritation. Moreover different surfactants bind to skin proteins to varying degrees. Cleansers that do not leave residual surfactants on the skin are therefore more desirable to many consumers. At least one test has been disclosed for evaluating the amount of dye and/or pigment binding to skin and evaluating the extent of skin adsorption of surfactant which interferes with dye and/or pigment binding. However there has not been a convenient way for the consumer to ascertain how a particular cleanser will interact with their skin using a particular cleansing method until now.

A diagnostic test is disclosed by Imokawa and Mishima, Contact Dermatitis 5:357-366, (1979) which uses dye to determine whether or not skin has appreciable amounts of adsorbed surfactant. The disclosed test uses dye solutions which are not convenient or appropriate when developing a convenient method intended for consumer use.

A convenient method for detecting and quantifying residual surfactants has been discovered that employs soluble or dispersible solid or semisolid films as dye and/or pigment carriers where the dye and/or pigment(s) have an affinity for either the skin or the surfactant left on the skin. Although not wishing to be bound to the following theory, it is believed that in a first case where a dye and/or pigment has an affinity for the skin but not for the residual surfactant of interest, application of the dye and/or pigment to skin with residual surfactant will result in skin with less coloration then to skin without the residual surfactant. In a second case where a dye and/or pigment has an affinity for the residual surfactant of interest but not for the skin, application of the dye and/or pigment to skin with residual surfactant will result in skin with more coloration then to skin without the residual surfactant. Both cases assume that neither the surfactant nor the reagent which removes the film/coating alters the skin itself in a way that changes the skin's propensity to interact with a given dye or pigment independently of the amount of surfactant adsorbed onto the skin.

SUMMARY OF THE INVENTION

In one aspect of the invention is a method for estimating the residual amount of a cleansing composition remaining on skin of a user after washing, including but not limited to the steps of:

a. treating an area of skin by applying the cleansing composition thereto wherein the cleansing composition contains at least about 1% by wt. of an anionic surfactant;

b. removing said cleansing composition from the treated area of the skin until there is no longer perception of any residual cleansing composition remaining on the treated area of the user's skin;

c. applying to the treated area of the skin, a solid or semi-solid film or coating that is soluble or dispersible in a first reagent, the film or coating containing at least 0.001% by wt. of dye and/or pigment(s), wherein said dye and/or pigment(s) are capable of adsorbing, reacting and/or associating with either the anionic surfactant or human or animal skin d. contacting the film or coating with sufficient first reagent effective to allow the dye and/or pigment contained therein to contact the treated area of the skin; and e. assessing the amount of dye and/or pigment adsorbed onto either the skin or residual surfactant upon the skin upon removal of the film or coating with the first reagent.

In another aspect of the invention is a diagnostic kit for estimating the residual amount of a cleansing composition containing one or more anionic surfactants remaining on the skin after removal of the cleansing composition, the kit including but not limited to the following:

a. a solid or semisolid film that is soluble or dispersible in a first reagent containing at least 0.001% by wt. of dye and/or pigment(s), wherein said dye and/or pigment(s) is/are capable of adsorbing, reacting and/or associating with either the anionic surfactant or human or animal skin;

b. instructions for applying the film to the skin and visualizing the residual adsorbed anionic surfactant on the skin after removal of the film; and c. a color gradation scale denoting the intensity of adsorbed dye and/or pigment on the skin corresponding with the approx. levels of residual cleansing composition on the skin.

Preferred embodiments of the invention will now be described by way of example with reference to the accompanying figures.

DETAILED DESCRIPTION OF THE INVENTION

Figure 1:
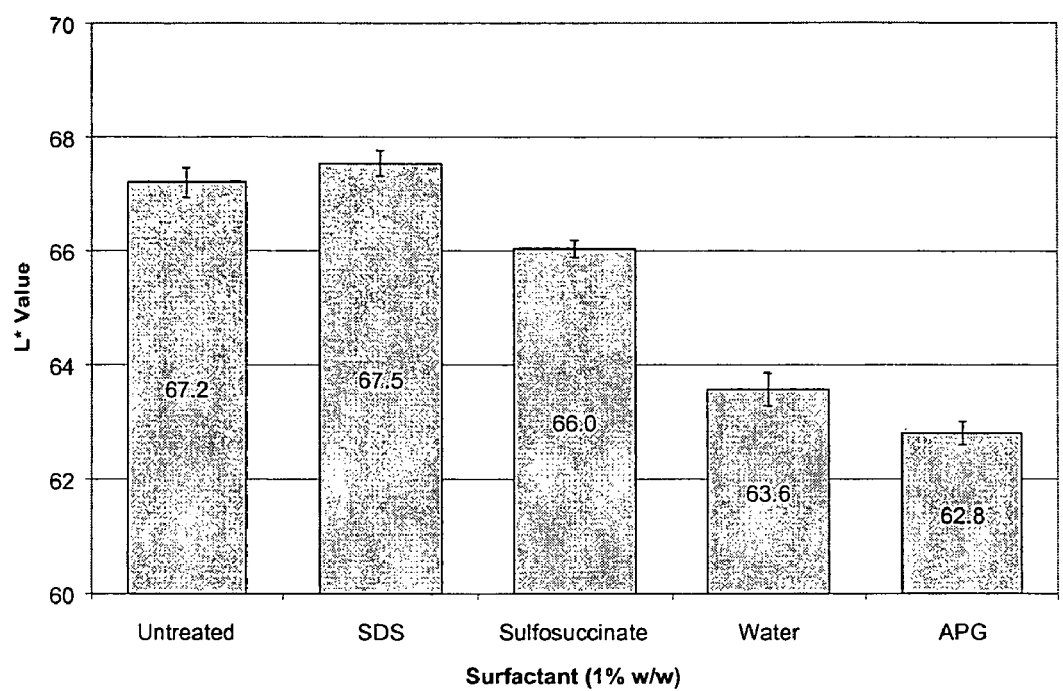
FIG. 1 is a bar graph depicting the color measurement (L*) of surfactant type binding using indigo carmine staining intensity of treated skin tested according to the procedure of Example 1.

In one aspect of the invention is a method for estimating the residual amount of a cleansing composition remaining on skin of a user after washing, including but not limited to the steps of:

a. treating an area of skin by applying the cleansing composition thereto wherein the cleansing composition contains at least about 1, 2, 3, 4 or 5% by wt. of an anionic surfactant;

b. removing said cleansing composition from the treated area of the skin (preferably by rinsing with water) until there is no longer perception of any residual cleansing composition remaining on the treated area of the user's skin (advantageously followed by pat drying the treated area);

c. applying to the treated area of the skin a solid or semi-solid film or coating that is soluble or dispersible in a first reagent, the film or coating containing at least 0.001% by wt. of dye and/or pigment(s) wherein said dye and/or pigment(s) is/are capable of adsorbing, reacting and/or associating with either the anionic surfactant or human or animal skin;, (e.g. indigo carmine, octadecyl fluorescein, beta carotene, lycopene and/or methylene blue and the like)

d. contacting the film or coating with sufficient first reagent effective to allow the dye and/or pigment contained therein to contact the treated area of the skin; and e. assessing the amount of dye and/or pigment adsorbed onto either the skin or residual surfactant upon the skin upon removal of the film or coating.

In one preferred embodiment, the dye and/or pigment adsorbed onto either the skin or residual surfactant upon the skin is further treated with sufficient second reagent having an affinity for the dye and/or pigment to remove excess dye and/or pigment. Advantageously the amount of dye and/or pigment adsorbed onto the treated area of the skin is visually compared to a control treated area of skin containing no adsorbed surfactant. Preferably the amount of dye and/or pigment adsorbed onto the treated area of the skin is compared to a control treated area containing no adsorbed surfactant by a quantitative energy reflectance and/or absorption method(s). More preferably the film is selected from a self-supporting film (such as a water, alcohol or oil soluble polymeric film) or a non-self-supporting coating (such as a temporary tattoo).

In a preferred embodiment, the cleansing composition contains at least 5% of anionic surfactant(s) having an individual zein value of greater than about 10, 20, 30, 40 or 50. Advantageously the cleansing composition contains one or more anionic surfactants selected from acyl glutamates, acyl peptides, sarcosinates, taurates, alkanoic acids and alkanoates, ester carboxylic acids, ether carboxylic acids, phosphoric acid esters and salts, acyl isethionates, alkylaryl sulfonates, alkyl sulfonates, sulfosuccinates, alkyl ether sulfates, or alkyl sulfates or a blend thereof.

Preferably the dye and/or pigment is present in the film in the concentration range of about 0.001 to 50 wt. % preferably at a lower limit of about 0.01, 0.05 or 0.1 to an upper limit of about 0.5, 1, 2, 3, 4, 5, 10, 20 or 30% by wt. More preferably the dye and/or pigment(s) is/are selected from one or more of the following classes: acid, basic, mordant, natural, solvent, direct, FD&C dyes, D & C dyes, Suitable pigments include those generally recognized as safe, and listed in C.T.F.A. Cosmetic Ingredient Handbook, First Edition, Washington D.C. (1988), incorporated herein by reference.

Advantageously, the film contains one or more of the following components: carbohydrate(s), protein(s), acrylamide(s), or quaternary modified compounds or blends thereof (advantageously starch, cellulose, hydroxypropyl trimonium guar, pullulan, gellan gum, polyquaternium-22, gelatin, polyacrylamide and the like). Preferably the reagent contains one or more of the following components: water, mono and/or polyhydric alcohol(s); polyol(s); mineral, glyceride and/or silicone oils, or a blend thereof.

In another aspect of the invention is a diagnostic kit for estimating the residual amount of a cleansing composition containing one or more anionic surfactants remaining on the skin after removal of the composition, the kit including but not limited to the following:

a. a solid or semisolid film that is soluble or dispersible in a first reagent, the film containing at least 0.001% by wt. of a dye and/or pigment(s), wherein said dye and/or pigment(s) is/are capable of adsorbing, reacting and/or associating with either the anionic surfactant or human or animal skin;, (e.g. indigo carmine, octadecyl fluorescein, beta carotene, lycopene and/or methylene blue and the like);

b. instructions for applying the film to the skin and visualizing the residual adsorbed anionic surfactant on the skin after removal of the film and optionally of excess dye and/or pigment(s); and c. a color gradation scale denoting the intensity of adsorbed dye and/or pigment on the skin corresponding with the approx. levels of residual cleansing composition on the skin.

Dyes and Pigments

Suitable dyes and/or pigments include various organic and inorganic dyes or pigments or blends thereof that have an affinity for and/or color the residual cleansing composition or the skin itself. Suitable organic pigments include azo, indigoid, triphenylmethane, anthraquinone, and xanthine dyes which are designated as D&C and FD&C (blues, browns, greens, oranges, reds, yellows, etc.). Inorganic pigments are generally insoluble metallic salts of certified color additives, referred to as lakes or iron oxides. Other suitable pigments are selected from the group of titanium dioxide, zinc oxide, and metallic lakes of cosmetic dyes or blends thereof. Suitable natural dyes include turmeric oleoresins, cochineal extracts, gardenia extracts, and natural colors derived from vegetable juices. Other specific examples of suitable natural dyes include, but are not limited to, beet extract, grape skin extract, and chlorophyll containing extracts (e.g. nettle extract, alfalfa extract and spinach extract). Suitable pigments include those generally recognized as safe, and listed in C.T.F.A. Cosmetic Ingredient Handbook, First Edition, Washington D.C. (1988), incorporated herein by reference. Specific examples are red iron oxide, yellow iron oxide, black iron oxide, brown iron oxide, ultramarine, FD&C Red, Nos. 2, 5, 6, 7, 10, 11, 12, 13, 30 and 34; FD&C Yellow No. 5, Red 3, 21, 27, 28, and 33 Aluminum Lakes, Yellow 5, 6, and 10 Aluminum Lakes, Orange 5 Aluminum Lake, Blue 1 Aluminum Lake, Red 6 Barium Lake, Red 7 Calcium Lake, and the like.

Reagent Soluble or Dispersible Solid or Semisolid Films:

In a preferred embodiment, a solid or semisolid film or coating that is soluble or dispersible in a first reagent is a useful means of delivering the dye(s) and/or pigment(s) to the skin as described above. A solid or semisolid film or coating that is soluble or dispersible in a first reagent is herein defined as that which dissolves or disperses over a period of time when contacted by the first reagent at 25 C. Upon film dissolution, the dye(s) and/or pigment(s) contained in the film or coating contact the skin area on which the film or coating has been placed and are visible. Advantageously this time can be in the range of about 0.5 to 10 seconds while contacted with the first-reagent. The time may be shortened if the first reagent is used at an elevated temperature. Release is here defined as allowing at least about 50% of the dye(s) and/or pigment(s) in the film to contact the skin next to the film in about 5 seconds when the film is contacted by a suitable first reagent having an affinity for the film at 25 C.

When the first reagent contains water, materials that may be used to make the water soluble or dispersible solid or semisolid films or coatings of this invention include well known water soluble or dispersible resins, such as pullulan, other water soluble/dispersible polysaccharides and derivatives thereof, water soluble/dispersible cellulosic derivatives and the like. Other suitable resins are described in Davidson and Sittig, Water - Soluble Resins, Van Nostrand Reinhold Company, New York (1968), herein incorporated by reference. The water-soluble or dispersible resin should have useful characteristics such as sufficient water solubility or dispersibility so as to quickly release the dye and/or pigment contained within the film, and sufficient strength and pliability in order to permit machine handling while trimming and packaging without tearing. Other preferred water-soluble or dispersible resins include polyvinyl alcohol, cellulose ethers, polyethylene oxide, starch, polyvinylpyrrolidone, polyacrylamide, polyvinyl methyl ether-maleic anhydride, polymaleic anhydride, styrene maleic anhydride, hydroxyethylcellulose, methylcellulose, polyethylene glycols, carboxymethylcellulose, polyacrylic acid salts, alginates, acrylamide copolymers, guar gum, casein, ethylene-maleic anhydride resin series, polyethyleneimine, ethyl hydroxyethylcellulose, ethyl methylcellulose, hydroxyethyl methylcellulose and the like.

Other useful films include those that are either oil soluble/dispersible, alcohol soluble/dispersible, or soluble/dispersible in any reagent(s) that is/are safe for contact with human or animal skin. Oils may consist of one or more mineral, glyceride, silicone or any other suitable oil or a blend thereof. Alcohols may include one or more monohydric or polyhyric alcohols, polyols or blends thereof and the like. Suitable film examples include water/alcohol-soluble or water/alcohol-dispersible polymers that can be fashioned into films such as octylacrylamide/acrylates/butylaminoethyl methacrylate copolymer neutralized with a base such as aminomethylpropanol, alcohol-soluble polyamides, polyethers of 2,2- bis(4-hydroxyphenyl)propane and epichlorohydrin, and the like. Suitable oil soluble polymers that can be used in films include vinyl polymers such as polymers derived from the polymerization of at least one monoethylenically unsaturated alkyl (meth) acrylic monomer, preferably, an alkyl (meth)acrylic acid ester (i.e., an alkyl acrylate or alkyl methacrylate), wherein the alkyl group has at least 4 carbon atoms (on average) and preferably no greater than 22 carbon atoms (on average), and at least one monoethylenically unsaturated poly(alkylene oxide) monomer, preferably, a monoethylenically unsaturated poly(alkylene oxide) (meth)acrylic monomer and the like. Depending on the properties of the resultant polymer, the monoethylenically unsaturated alkyl (meth) acrylic acid esters used to prepare the polymer can have just short alkyl groups (e.g., at least 4 carbon atoms (on average) and preferably no greater than 14 carbon atoms (on average)), or just long alkyl groups (e.g., at least 15 carbon atoms (on average) and preferably no greater than 22 carbon atoms (on average)), or mixtures of monoethylenically unsaturated alkyl (meth)acrylic acid esters with short alkyl groups can be used in combination with monoethylenically unsaturated alkyl (meth)acrylic acid esters with long alkyl groups (e.g., terpolymers). The alkyl group can optionally contain heteroatoms (e.g., N, O, or S) and can be linear, branched, or cyclic. Other suitable vinyl polymers include polyethylene having a molecular weight of 2000 to 8000, polystyrene or poly alpha methylstyrene, block copolymers of styrene with ethylene, propylene and/or butalene, copolymers of polyvinylpyrrolidone with polyethylene and the like.

Polymers such as cellulose and starch polymeric derivatives that are oil soluble, such a dextrin esters, e.g. dextrin palmitate or other oil-soluble polymers that may be fashioned into films may also be used.

Temporary tattoos

In a second preferred embodiment, a temporary tattoo may be advantageously employed to ascertain the residual surfactant level on the skin. The dye(s) and/or pigment(s) will advantageously have an affinity for either the surfactant or the skin and will be incorporated in the temporary tattoo. There are three principle types of temporary tattoo which differ in the way they are applied to the skin. In a non-limiting manner, it is useful to classify temporary tattoos as: 1) those which are hand-painted or drawn directly on the skin; 2) those which are printed (or hand- painted or drawn) onto a substrate and then transferred to the skin some time later; and 3) those which are printed (or hand- painted or drawn) onto a transparent substrate which is subsequently adhered onto the skin. Preferably the transparent substrate is soluble or dispersible in water, alcohol, oil or another reagent that is safe for skin contact.

For a type 1 temporary tattoo, the artwork is applied to the skin with brushes and/or pens or similar implements, using inks or dye(s) and/or pigments, in a fashion analagous to making an illustration on paper. A stencil can be used. For a type 2 temporary tattoo, the artwork is usually printed in ink or dye and/or pigment onto a substrate (such as paper) having properties which allow the artwork to become dissociated from the substrate, some time after the printing, and transferred to skin (such examples have alternative names such decalcomania, decal or transfer). This transference is most commonly achieved by placing the printed substrate on the skin with the substrate uppermost and then wetting the substrate and applying gentle pressure before peeling off the substrate, leaving the artwork adhered to the skin. Clearly, the substrate, inks and dye and/or pigments must be selected such that they have properties which are appropriate to the transference procedure. Alternatively, there may be a transparent layer which covers the surface of the substrate and on top of which the artwork is printed. In this case, the transparent layer is transferred to the skin along with the artwork and thereafter forms a protective cover for the artwork, being uppermost on. the skin when the substrate is peeled away. Alternatively, a transparent protective layer may be applied to the tattoo after transfer of the artwork to the skin by covering the artwork with a strip of transparent material or else by applying the transparent layer in the form of a solution from which the layer is deposited on the tattoo after evaporation of the solvent. A transparent protective layer may also be applied to a type 1 temporary tattoo by these methods. For a type 3 temporary tattoo, the artwork is usually printed in ink or dye and/or pigment onto a transparent substrate which has an adhesive area that exceeds, overlaps or surrounds the artwork and assists, or is responsible for, its adherence to the skin (these may be alternatively called stickers). A type 3 temporary tattoo is adhered onto the skin such that the artwork is in contact with the skin and the transparent substrate often provides a protective adhesive layer.

A temporary tattoo (of any type) which is to be used for skin testing according to the invention may also be produced so that certain designated areas of the artwork contain different test dye and/or pigment compounds. Different areas could also contain the same test dye and/or pigment compound or material but at different concentrations. The person carrying out the test would in one embodiment keep a careful record or "tattoo map" detailing the precise distribution of the test dye and/or pigment materials in the tattoo. After the time allotted for the test, the tattoo may be partially or completely removed with an appropriate reagent or blend of reagents and the skin underneath examined for any signs of reaction or adsorption of the dye and/or pigment. Comparing signs of residual surfactant or the lack thereof (e.g. skin coloration) with the map will enable the estimation (and optionally the distribution) of the residual surfactants on the skin.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

EXAMPLE: 1

Figure 2:
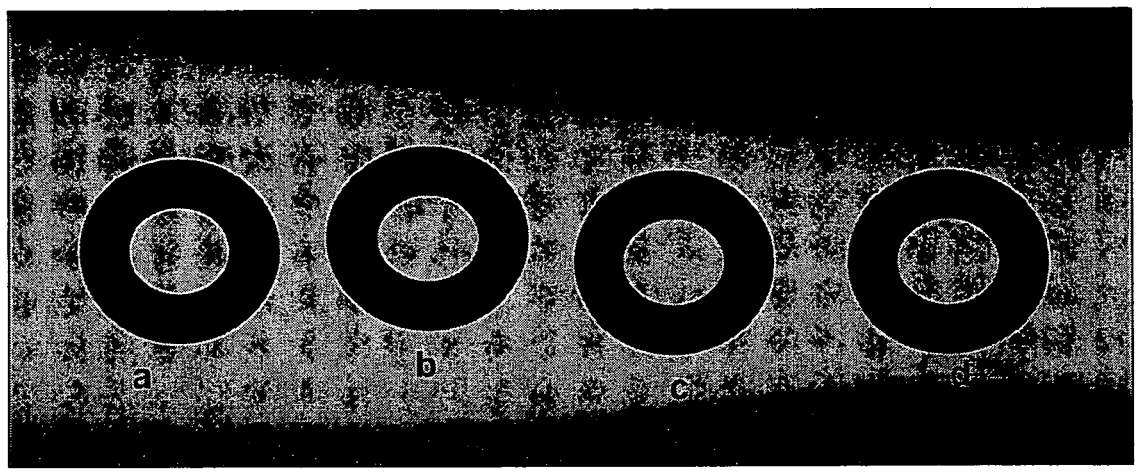
FIG. 2 is a photograph of a subject's forearm tested with various surfactant solutions according to the procedure of Example 1 that is depicted in FIG. 1.
Figure 3:
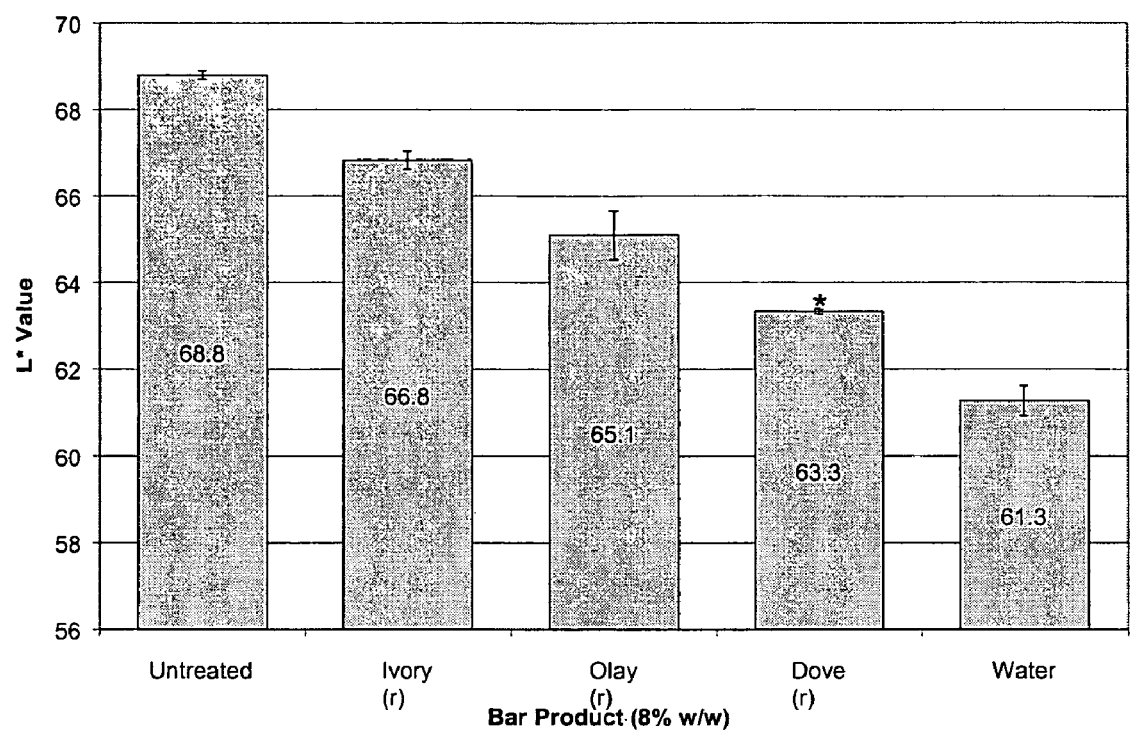
FIG. 3 is a bar graph depicting the color measurement (L*) of surfactant binding using commercially available toilet bars and indigo carmine staining intensity of treated skin tested according to the procedure of Example 1.
Figure 4:
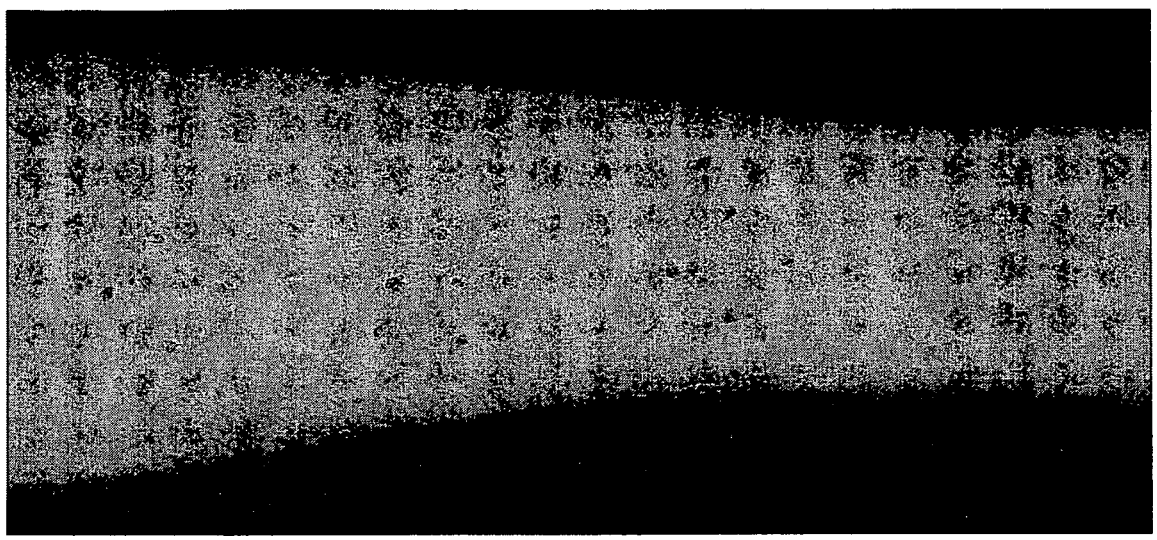
FIG. 4 is a photograph of a subject's forearm tested with various commercially available toilet bars according to the procedure of Example 1 that is depicted in FIG. 3.

Indigo carmine (2-(1,3-Dihydro-3-oxo-5-sulfo-2H-indol-2-ylidene)-2,3-dihydro-3-oxo-1H-indole-5-sulfonic acid disodium salt), an acid dye also known as FD&C Blue No. 2 (C.I. 73015), was employed in solution form to compare levels of residual surfactants remaining on the skin of three individual panelists after cleansing using both pure surfactant sample solutions and also samples of various commercially available toilet bars on multiple sites of their forearms according the procedure described below and the results are summarized in FIGS. 1 to 4 and Table 1. It was found that the dye coloration intensity increased with decreasing surfactant binding i.e. sodium dodecyl sulfate (SDS) (least stain uptake) >Sulfosuccinate >Water >Alkyl polyglucoside (APG) (most stain uptake). While not wishing to be bound by the following theory, it is believed that lipid removal by APG directly from the skin results in exposure of more skin protein binding sites to the dye, hence the greater intensity of coloration independent of surfactant adsorbtion. Another way of expressing the foregoing sequence (except for APG) is as follows: a. Little to no staining: Greatest surfactant binding; b. Weak staining: Moderate surfactant binding; c. Strong staining: Less surfactant binding; d. Strong staining: Water Control. The actual skin staining results are illustrated in FIG. 2.

Especially indicative of surfactant/dye binding is the b* value, the lower the number means the skin is bluer i.e. as the b* scale decreases the color changes from yellow to blue so a lower number means bluer. It was expected that the water treated site should have the lowest number as this situation allows for the most dye molecules to bind to the skin (in the absence of adsorbed surfactant). The untreated site, which had no stain applied, was expected to have the largest b* value (most yellow). Since soap molecules are known to bind to most of the skin proteins there is little opportunity for the dye to bind to the skin. The soap treated site will therefore be similar to the untreated control site. Dove(r) was found to be slightly better than Olay(r) with respect to surfactant binding to the skin.

Expressed in order of increasing intensity of dye staining, the results of the toilet bar testing are as follows: Ivory® Little to no staining: (Greatest surfactant binding); Dove® Moderate staining (Less surfactant binding); Olay® Moderate staining: (Less surfactant binding); and Water—Strongest staining: Water Control (no surfactant binding). While not wishing to be bound by the following theory, it is believed that soap binds to the skin more strongly than sodium cocoyl isethionate (SCI) found in syndet toilet bars such Dove(r) and Olay(r). Soap is also known to be more irritating than SCI.

Note: Ivory® and Olay® toilet bars are manufactured by Procter & Gamble Inc. (Cincinnati, OH) and Dove® toilet bars are manufactured by Unilever Inc. (Greenwich, CT.)

Indigo Carmine Forearm Washing Procedure
 Treat volar forearms (3.14 cm2 area) with 2 ml of surfactant/product solution or slurry for 2 minutes, e.g.
  1% w/w surfactant (SDS, Sulfosuccinate, APG)
  8% w/w bar slurry (Ivory (r), Dove (r), Olay (r))
 Remove surfactant and rinse site with 2 ml of DI water (at approx. 23 C), then repeat rinse step for bars.
 Pat area dry
 Apply 2 ml of 1% indigo carmine dye (aqueous) for 1 minute
 Remove dye and rinse site with 2 ml of DI water (at approx. 23 C)
 Pat area dry
 Obtain digital images with a conventional digital camera.
 Measure l*a*b* values at test sites using CR-10 chromameter (Minolta CM 508D spectrophotometer)

EXAMPLE 2

Samples of a commercially available water dissolvable film (1) comprised of Pullulan and containing a food grade dye (FD&C Green No. 3) were applied to the skin after cleansing with several cleansers according to Table 2, using the procedure described below. The results of the study are provided in table 1.

TABLE 1

L*, a*, and b* colorimetric skin values of three panelists whose forearms were treated in several locations with selected toilet bars vs. water and a control according to the forearm washing procedure described below.

| | | Panelist 1 | | | Panelist 2 | | | Panelist 3 | | |
|---|---|---|---|---|---|---|---|---|---|---|
| | | L* | A* | B* | L* | A* | B* | L* | A* | B* |
| site 1 | Olay ® Bar | 64 | 1.63 | 13.55 | 60.42 | 1.53 | 16.35 | 59.37 | 4.97 | 15.75 |
| | (5%) | 63.57 | 1.83 | 13.43 | 60.96 | 1.85 | 13.75 | 58.8 | 5.64 | 16.15 |
| | | 62.82 | 1.79 | 13.49 | 60.76 | 2.03 | 13.86 | 58.53 | 5.63 | 16.31 |
| | Ave. | 63.46 | 1.75 | 13.49 | 60.71 | 1.80 | 14.65 | 58.90 | 5.41 | 16.07 |
| Site 2 | Dove ® Bar | 63.57 | 0.89 | 11.68 | 59.63 | 1.68 | 13.17 | 60 | 4.87 | 14.4 |
| | (5%) | 62.78 | 0.51 | 10.57 | 61.48 | 1.12 | 12.77 | 59.83 | 4.87 | 14.56 |
| | | 62.84 | 0.02 | 10.59 | 61.96 | 1.45 | 13.89 | 60.06 | 4.85 | 14.56 |
| | Ave. | 63.06 | 0.47 | 10.95 | 61.02 | 1.42 | 13.28 | 59.96 | 4.86 | 14.51 |
| Site 3 | water treated | 59.87 | −1.94 | 7.46 | 59.55 | 0.36 | 11.58 | 58.74 | 1.6 | 11.57 |
| | | 59.97 | −2.26 | 7.72 | 59.13 | 0.47 | 11.62 | 59 | 1.55 | 11.38 |
| | | 60.24 | −2.25 | 7.82 | 59.71 | 0.15 | 11.48 | 58.8 | 1.49 | 11.58 |
| | Ave. | 60.03 | −2.15 | 7.67 | 59.46 | 0.33 | 11.56 | 58.85 | 1.55 | 11.51 |
| Site 4 | untreated | 66.37 | 4.8 | 14.7 | 63.52 | 7.49 | 16.43 | 61.32 | 7.72 | 17.21 |
| | | 65.26 | 4.75 | 14.48 | 63.35 | 6.21 | 15.84 | 60.73 | 8.8 | 18.12 |
| | | 66.19 | 4.48 | 14.59 | 64.32 | 5.59 | 15.47 | 60.8 | 9.28 | 18.9 |
| | Ave. | 65.94 | 4.68 | 14.59 | 63.73 | 6.43 | 15.91 | 60.95 | 8.60 | 18.08 |
| Site 5 | Soap (Zest ®) | | | | | | | 56.3 | 11.45 | 16.99 |
| | | | | | | | | 57.17 | 10.32 | 16.7 |
| | | | | | | | | 56.76 | 11.04 | 16.9 |
| | Ave. | | | | | | | 56.74 | 10.94 | 16.86 |

Note (1) Listerine PocketPaks® (D Oral Care Strips (available from Warner-Lambert Company Inc.

TABLE 2

| Tested | Avg *b | |
|---|---|---|
| Dove(r) (5%) | 12.3 | high stain |
| Ivory(r) (5%) | 17 | low stain |
| Untreated | 18.5 | low stain |

Method:
Listerine® strip application

Treat volar forearms (3.14 cm2 area) with 2 ml of surfactant/product solution or slurry for 2 minutes, e.g.
1% w/w surfactant (SDS, Sulfosuccinate, APG).
8% w/w bar slurry (Ivory(r), Dove(r), Olay(r)).
Remove surfactant and rinse site with 2 ml of DI water (at approx. 23 C) (repeat rinse step for bars).
Pat area dry.
After arms have been treated with specified products (see above procedure for example 1) take approximately 5 ml's of water (at approx. 23 C)and wet treated area.
Gently place a dry test strip over treated and wetted area on forearm.
Gently pat test strip against skin with finger
Allow strip to remain in contact with forearm for 3 minutes. (or until arm has air dried).
After three minutes place area of forearm with test strip in running stream of warm water (approx. 10 seconds at 40-50 C) and remove from the skin the remainder of the strip which has not dissolved.
Pat dry.

EXAMPLE 3

TABLE 4

| | Avg *b | |
|---|---|---|
| Olay ® Bar (5%) | 12 | low-mod value - mod-high stain |
| Dove ® Bar (5%) | 10 | Low value - mod high stain |
| water treated | 8 | Lowest value - most stain |
| untreated | 16 | Highest Value - low stain |
| Soap (e.g. Zest ®) | 16 | Highest Value - low stain |

Zein Test Method

The cleanser containing the anionic surfactant to be tested preferably have a zein solubility of greater than 10, 20, 30, 40 or 50 using the zein solubility method set forth below. The greater the zein score, the more harsh the cleansing base/surfactant is considered to be. This method involves measuring the solubility of zein (corn protein) in cleansing base solutions containing the anionic surfactant of interest as follows:

0.3 g of cleansing base and 29.7 g of water are mixed thoroughly. To this is added 1.5 g of zein, and mixed for 1 hour. The mixture is then centrifuged for 30 minutes at 3000 rpm. After centrifugation, the pellet is extracted, washed with water, and dried in a vacuum oven for 24 hours until substantially all the water has evaporated. The weight of the dried pellet is measured and percent zein solubilized is calculated using the following equation:

% Zein solubilized=100 (1-weight of dried pellet/1.5).

The % Zein is further described in the following references: E. Gotte, Skin compatibility of tensides measured by their capacity for dissolving zein protein, Proc. IV International Congress of Surface Active Substances, Brussels, 1964, pp 83-90.

While this invention has been described with respect to particular embodiments thereof, it is apparent that numerous

TABLE 3

Composition of a suitable type 1 temporary tattoo solution.

| Ingredient INCI Name | Trade Name | % Active (of Raw) | % of Ingredient in Formula AS IS | % Active (in final formula) | Range Formula | Preferred | Most preferred |
|---|---|---|---|---|---|---|---|
| Polyquaternium-22 | Merquat 280 | 41% | 45% | 18.4500% | 0 to 40% | 5 to 30% | 15 to 20% |
| Hydroxyethylcellulose | Natrosol 250 HMR | 1% | 45% | 0.4500% | 0 to 2% | 0 to 1% | 0.2 to 0.8% |
| Indigo Carmine | | | | | 0.01 to 10% | 0.1 to 20 | 1 to 5% |
| Water | | | | | QS to 100% | | |

Procedure:

A type 1 temporary tattoo having the composition given in table 3 may be painted on treated skin using a decorative stencil (e.g. shaped like a butterfly). Prior to the application of the tattoo, the skin is treated with various toilet bars described in table 4. The site of the temporary tattoo is then exposed to warm (approx 50-60 C) running water for about 30 seconds and the skin's I* a* and b* properties are measured with a suitable spectrophotometer as described above. It is expected that the results listed in table 4 will be obtained.

other forms and modifications of the invention will be obvious to those skilled in the art. The appended claims and this invention generally should be construed to cover all such obvious forms and modifications which are within the true spirit and scope of the present invention.

We claim
1. A method for estimating the residual amount of a cleansing composition remaining on skin after washing, comprising the steps of:
   a. treating an area of skin by applying the cleansing composition thereto wherein the cleansing composition contains at least 1% by wt. of an anionic surfactant;

b. removing said cleansing composition from the treated area of the skin until there is no longer any perception of residual cleansing composition remaining on the treated area of the skin;

c. applying to the treated area of the skin a solid or semi-solid film or coating, that is soluble or dispersible in a first reagent, the film or coating containing an effective amount of dye and/or pigment(s), wherein said dye and/or pigment(s) are capable of adsorbing, reacting and/or otherwise associating with either the anionic surfactant or human or animal skin and is/are present in a sufficient amount capable of detection in its associated state on the skin;

d. contacting the film or coating with sufficient first reagent effective to allow the dye and/or pigment contained in the film or coating to contact the treated area of the skin; and e. assessing the amount of dye and/or pigment adsorbed onto either the skin or residual surfactant upon the skin upon removal of the film or coating.

2. The method of claim 1 wherein the dye and/or pigment adsorbed onto either the skin or residual surfactant upon the skin is further treated with a sufficient amount of a second reagent to remove excess dye and/or pigment wherein the second reagent has an affinity for the dye and/or pigment.

3. The method of claim 1 wherein the amount of dye and/or pigment adsorbed onto the treated area of the skin is visually compared to a control treated area of skin containing no adsorbed surfactant.

4. The method of claim 1 wherein the amount of dye and/or pigment adsorbed onto the treated area of the skin is compared to a control treated area containing no adsorbed surfactant by a quantitative energy reflectance and/or absorption method(s).

5. The method of claim 1 wherein the film or coating is selected from a self-supporting film or a non-self-supporting coating.

6. The method of claim 1 wherein the cleansing composition contains at least 5% of anionic surfactant(s) having an individual zein value of greater than 10.

7. The method of claim 1 wherein the cleansing composition contains one or more anionic surfactants selected from acyl glutamates, acyl peptides, sarcosinates, taurates, alkanoic acids and alkanoates, ester carboxylic acids, ether carboxylic acids, phosphoric acid esters and salts, acyl isethionates, alkylaryl sulfonates, alkyl sulfonates, sulfosuccinates, alkyl ether sulfates, or alkyl sulfates or a blend thereof.

8. The method of claim 1 wherein the dye and/or pigment is present in the film in the concentration range of about 0.001 to 50 wt. %.

9. The method of claim 1 wherein the dye and/or pigment(s) is/are selected from one or more of the following classes: acid, basic, mordant, natural, solvent, direct, FD&C dyes, D & C dyes.

10. The method of claim 1 wherein the film contains one or more of the following components: carbohydrate(s), protein(s), acrylamide(s), or quaternary modified compounds or blends thereof.

11. The method of claim 2 wherein the first reagent may be the same or different compared to the second reagent and wherein either the first or second reagent or both contain one or more of the following components: water, mono and/or polyhydric alcohol(s); polyols, mineral, glyceride and/or silicone oils, or a blend thereof.

* * * * *